US008109907B2

(12) United States Patent
Tsukada et al.

(10) Patent No.: US 8,109,907 B2
(45) Date of Patent: Feb. 7, 2012

(54) CONTINUOUS DRUG SOLUTION INFUSION DEVICE

(75) Inventors: Osamu Tsukada, Ueda (JP); Yasuhiko Nakajima, Hiratsuka (JP)

(73) Assignee: Tsukada Medical Research Co., Ltd.

( * ) Notice: Subject to any disclaimer, the term of this patent is extended or adjusted under 35 U.S.C. 154(b) by 97 days.

(21) Appl. No.: 12/373,030

(22) PCT Filed: Jul. 11, 2006

(86) PCT No.: PCT/JP2006/313715
§ 371 (c)(1),
(2), (4) Date: Jan. 8, 2009

(87) PCT Pub. No.: WO2008/007422
PCT Pub. Date: Jan. 17, 2008

(65) Prior Publication Data
US 2009/0247950 A1    Oct. 1, 2009

(51) Int. Cl.
*A61M 37/00*    (2006.01)
(52) U.S. Cl. ........................................................ 604/132
(58) Field of Classification Search .................. 604/132
See application file for complete search history.

(56) References Cited

U.S. PATENT DOCUMENTS

| 4,318,400 A | 3/1982 | Peery et al. | |
|---|---|---|---|
| 5,011,477 A * | 4/1991 | Winchell et al. | 604/132 |
| 5,080,652 A * | 1/1992 | Sancoff et al. | 604/132 |
| 5,211,632 A * | 5/1993 | Tsukada | 604/132 |
| 2006/0122562 A1 * | 6/2006 | Needle et al. | 604/185 |

FOREIGN PATENT DOCUMENTS

| EP | 0473781 A1 | 3/1992 |
|---|---|---|
| JP | 38-28958 | 12/1905 |
| JP | 43-014926 Y1 | 6/1968 |
| JP | 56-102252 A | 8/1981 |
| JP | 03-505538 A | 12/1991 |
| JP | 43-12517 A | 11/1992 |
| JP | 11-280465 A | 10/1999 |
| JP | 2003-111839 A | 4/2003 |
| WO | WO-90/12609 A1 | 11/1990 |
| WO | WO-91/12835 A1 | 9/1991 |
| WO | WO03030970 A1 | 4/2003 |

* cited by examiner

*Primary Examiner* — Nicholas Lucchesi
*Assistant Examiner* — Jason Flick
(74) *Attorney, Agent, or Firm* — Harness, Dickey & Pierce, P.L.C.; Michael E. Hilton

(57) ABSTRACT

A continuous drug solution infusion device is provided that is capable of administering a drug solution into a patient's body for a predetermined period of time substantially at a predetermined flow rate from the beginning to end of the drug solution infusion by suppressing the change in pressure from the beginning to end of the infusion. The continuous drug solution infusion device has at least two tubular members disposed in series along an infusion path for a drug solution and at least one expandable/contractible tubular member disposed between the tubular members.

20 Claims, 7 Drawing Sheets

CONTINUOUS DRUG SOLUTION INFUSION DEVICE

This application is a 371 U.S. National Stage of International Application No. PCT/JP2006/313715, filed Jul. 11, 2006, which is hereby incorporated herein in its entirety.

TECHNICAL FIELD

The present invention relates to a continuous drug solution infusion device for continuously administering a drug solution into a patient's body. More particularly, the present invention relates to a continuous drug solution infusion device capable of continuously administering a drug solution into a patient's body substantially at a predetermined flow rate from the beginning to end of the infusion.

BACKGROUND ART

There are cases where it is necessary to administer a drug, such as an analgesic, a sedative, an antipyretic, or a nutritional supplement, into a patient's body continuously for a predetermined period of time. As a continuous drug solution infusion device used for this purpose, there has heretofore been known a device including a single tube having a drug solution inlet part and a drug solution outlet part attached respectively to both ends thereof. The device further includes a balloon made of an elastic material, e.g. a rubber material, and secured at both ends thereof to the outer periphery of the tube. The respective insides of the tube and the balloon are communicated with each other through a communicating hole provided in the tube. With this continuous drug solution infusion device, a drug solution is stored into the balloon from the drug solution inlet part through the communicating hole, and the stored drug solution is forced to flow out through the communicating hole by the contracting force of the expanded balloon and continuously infused into the patient's body from the drug solution outlet part. The drug solution outlet part is provided with a control passage to suppress a high-rate flow of drug solution caused by the pressure of the balloon and to administer the drug solution into the patient's body at a predetermined low flow rate over a long period of time. With the conventional continuous drug solution infusion device, however, the flow rate is high at the beginning of the infusion and decreases with the passage of time. Therefore, it is difficult to infuse the drug solution into the patient's body substantially at a predetermined flow rate from the beginning of the infusion. The reason for this is as follows. Because the balloon is secured to a single tube, it can expand only in the radial direction of the tube and cannot expand in the axial direction of the tube. Accordingly, the pressure of the balloon changes to a considerable extent from the time of expansion to the time of contraction.

Meanwhile, there is a continuous drug solution infusion device in which one end of a balloon is secured to a single tube to allow the balloon to expand and contract in both the radial and axial directions of the tube. With this device, however, a protection cover secured to the tube needs to be increased in the axial dimension in order to allow the expansion of the balloon in the axial direction, which requires a relatively large accommodating space at the time of storage and transportation. In addition, there is an increase in the cost of disposing of the device as a medical waste.

DISCLOSURE OF THE INVENTION

Problems to be Solved by the Invention

An object of the present invention is to provide a continuous drug solution infusion device capable of administering a drug solution into a patient's body for a predetermined period of time substantially at a predetermined flow rate from the beginning to end of the drug solution infusion by suppressing the change in pressure from the beginning to end of the infusion. Another object of the present invention is to provide a continuous drug solution infusion device that is normally compact in size and superior in accommodatability and disposability.

Means for Solving the Problems

The invention of claim 1 provides a continuous drug solution infusion device having at least two tubular members disposed in series along an infusion path for a drug solution and at least one expandable/contractible tubular member disposed between the tubular members.

According to the invention of claim 2, the tubular members include a first tubular member disposed at an inlet-side end of the drug solution infusion path and a second tubular member disposed at an outlet-side end of the drug solution infusion path. The expandable/contractible tubular member is a single expandable/contractible tubular member disposed between the first and second tubular members. With this structure, the expandable/contractible tubular member can be expanded and contracted not only in the radial direction but also in the axial direction. Accordingly, it is possible to reduce the change in pressure over a period of time from the expansion to contraction of the expandable/contractible tubular member.

The invention of claim 3 has the following features in addition to those of the invention of claim 1 or 2. That is, the continuous drug solution infusion device further has a protection cover comprising an outer cover and an inner cover disposed inside the outer cover. The protection cover is provided on the tubular members at both ends of the drug solution infusion path so as to cover the expandable/contractible tubular member. With this arrangement, the expandable/contractible tubular member can be protected when it is expanded. Because the protection cover comprises axially divided outer and inner covers, when the continuous drug solution infusion device is in a normal inoperative state, the outer and inner covers can be positioned close to each other. Consequently, the device can be reduced in size in the axial direction. At the time of filling a drug solution, the outer cover and the inner cover can move away from each other to allow the expandable/contractible tubular member to expand in the axial direction.

The invention of claim 4 has the following feature in addition to those of the invention of claim 3. That is, the protection cover includes drug solution measuring means. This arrangement makes it possible to measure the amount of drug solution remaining in the device and to facilitate the drug solution administration control.

The invention of claim 5 has the following features in addition to those of the invention of claim 4. That is, the protection cover is made of a transparent or semitransparent material. The drug solution measuring means comprises graduations provided on one of the outer and inner covers, and a reference line provided on the other of the outer and inner covers in correspondence to the position of the graduations. With this arrangement, the change in the amount of drug solution remaining in the device can be measured easily by the relative movement between the graduations and the reference line when the outer cover and the inner cover move toward each other as the drug solution flows out.

The invention of claim 6 has the following feature in addition to those of the invention of claim 4. That is, the drug solution measuring means comprises a slit provided with graduations that is provided on the outer cover, and a reference line provided on the inner cover in correspondence to the position of the slit. With this arrangement, the change in the amount of drug solution remaining in the device can be measured easily by the relative movement between the reference line seen through the slit and the graduations marked along the slit when the outer cover and the inner cover move toward each other as the drug solution flows out. In addition, the protection cover need not be formed from a transparent or semitransparent material.

The invention of claim 7 has the following feature in addition to those of the invention of any one of claims 3 to 6. That is, the outer and inner covers of the protection cover include separation-preventing stoppers which are engageable with each other. This arrangement makes it possible to prevent the outer cover and the inner cover from completely separating from each other in the axial direction.

The invention of claim 8 has the following feature in addition to those of the invention of any one of claims 3 to 7. That is, the outer cover has at least one flat portion in a section thereof taken in the radial direction of the tubular members. With this arrangement, rolling of the device can be prevented.

The invention of claim 9 has the following features in addition to those of any one of claims 3 to 8. That is, the inner cover has a flat portion corresponding to a flat portion of the outer cover. The inner cover is fitted in the outer cover with their flat portions facing each other. This arrangement makes it possible to prevent rolling of the device and to prevent the relative rotation between the outer cover and the inner cover.

The invention of claim 10 has the following features in addition to those of any one of claims 3 to 9. That is, the outer cover has a polygonal section taken in the radial direction, and the inner cover has a polygonal section so as to fit in the outer cover. With this arrangement, rolling of the device and the relative rotation between the outer and inner covers can be prevented even more effectively.

Advantages of the Invention

According to the continuous drug solution infusion device of the present invention, it is possible to reduce the change in pressure over a period of time from the expansion to contraction of the expandable/contractible tubular member. Therefore, the drug solution can be administered into the patient's body for a long period of time substantially at a predetermined flow rate from the beginning to end of the infusion.

According to the continuous drug solution infusion device of the present invention, the axial dimension of the device in a normal inoperative state can be reduced. Therefore, it is possible to obtain a continuous drug solution infusion device that is easy to store and transport and has a reduced cost of disposing of the device as a medical waste.

According to the continuous drug solution infusion device of the present invention, it is possible to readily measure the amount of drug solution remaining in the device and hence possible to facilitate the drug solution administration control.

LEGEND

Figure 1:
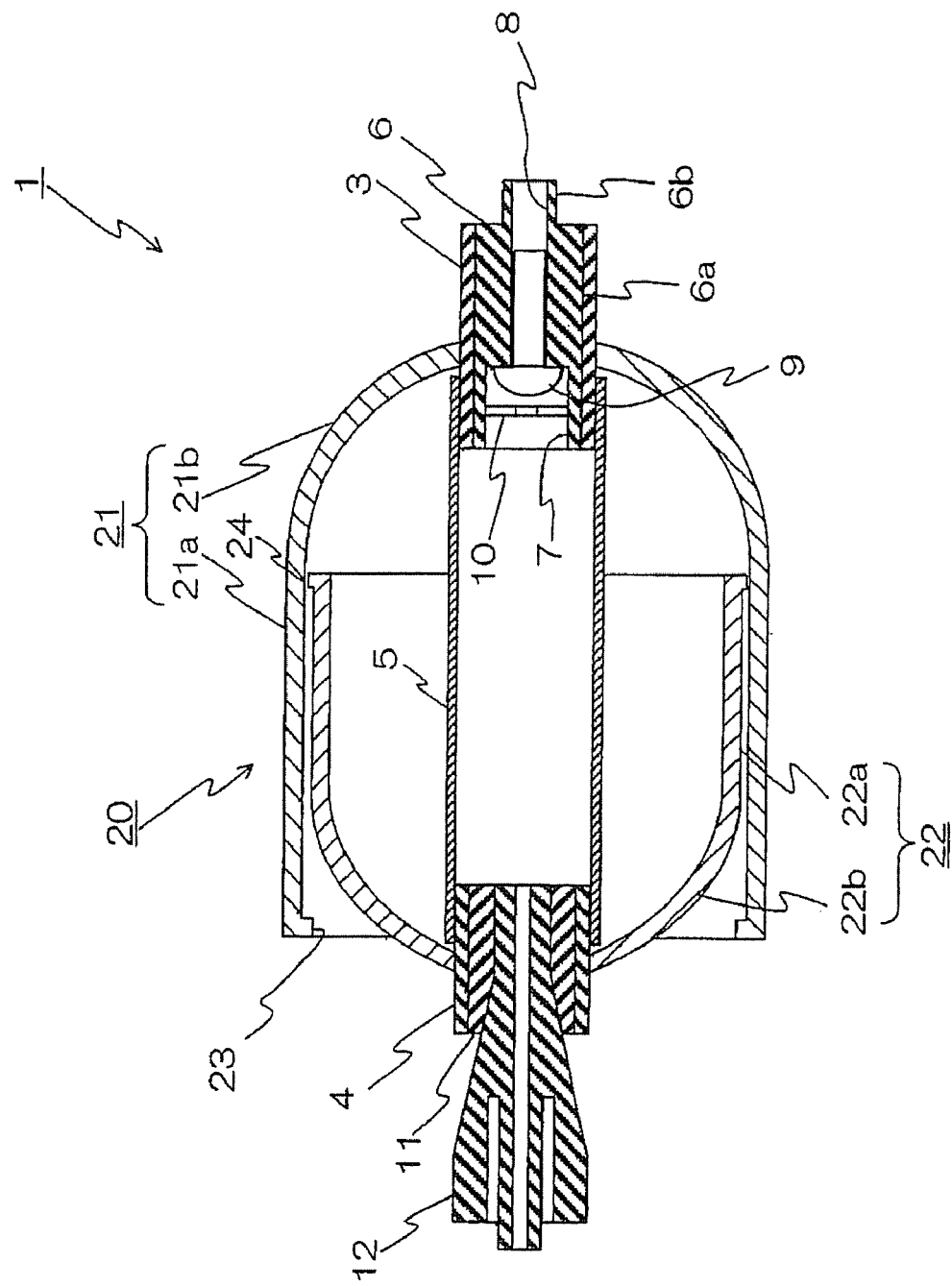
FIG. 1 is an axial sectional view of a continuous drug solution infusion device according to the present invention taken along the line I-I in FIG. 5, showing an expandable/contractible tubular member in a contracted state.

1: continuous drug solution infusion device
3: first tubular member
4: second tubular member
5: expandable/contractible tubular member
6: drug solution filling part
6a: large-diameter portion
6b: small-diameter portion
7: recess
8: central drug solution passage
9: valve member (check valve)
10: retaining member
11: drug solution outlet part
12: male lure-lock connector
20: protection cover
21, 41, 51: outer cover
22, 42, 52: inner cover
21a, 22a: tubular portion
21b, 22b: curved portion
23, 24: separation-preventing stopper
25, 27: graduations
26, 29: reference line
28: slit
30: flexible tube
31: clamp

PREFERRED EMBODIMENT OF THE INVENTION

Overall Summary

An embodiment of the continuous drug solution infusion device according to the present invention will be explained with reference to FIGS. 1 to 8.

Figure 2:
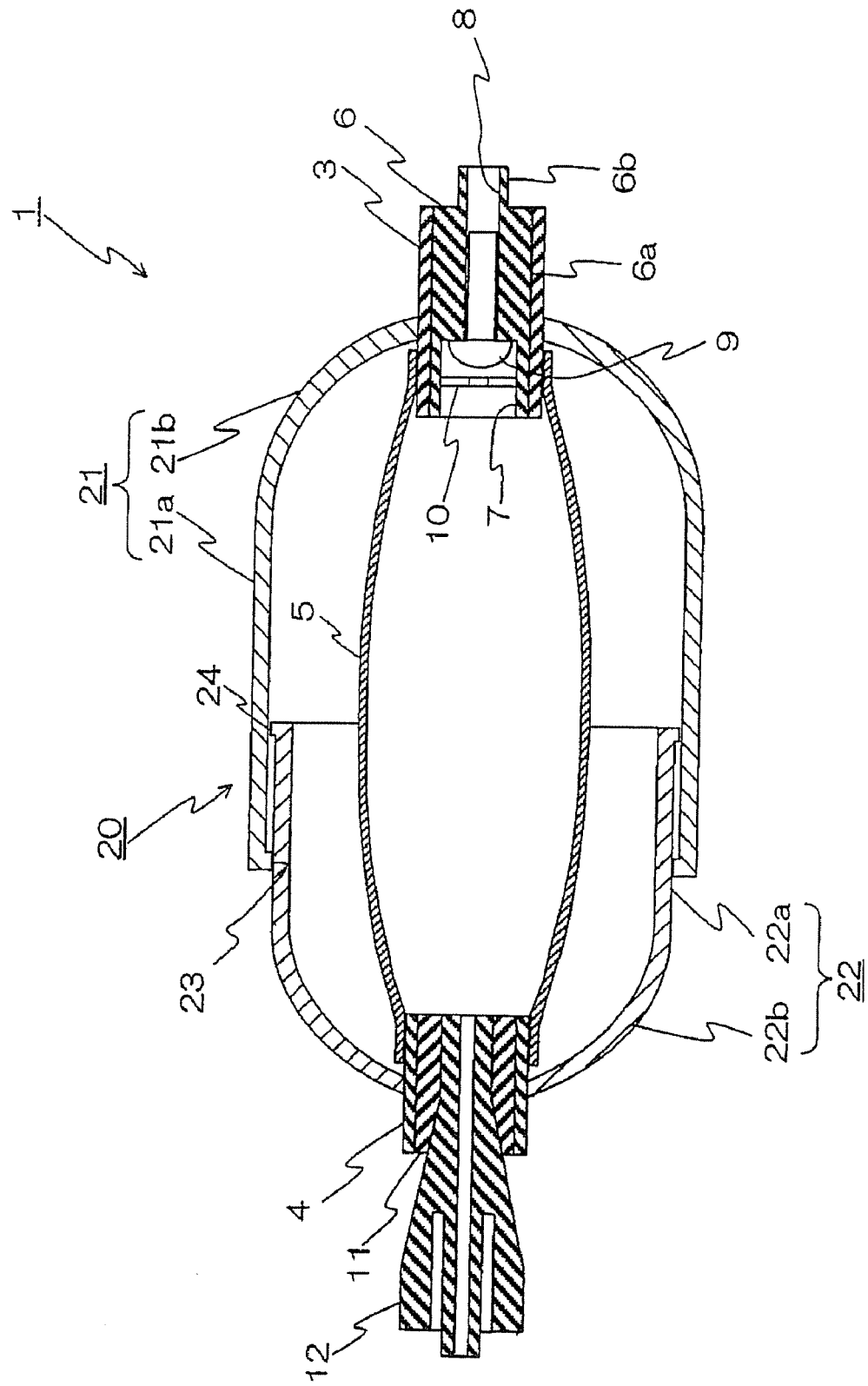
FIG. 2 is an axial sectional view of the continuous drug solution infusion device according to the present invention taken along the line I-I in FIG. 5, showing the expandable/contractible tubular member in a radially and axially expanded state.
Figure 3:
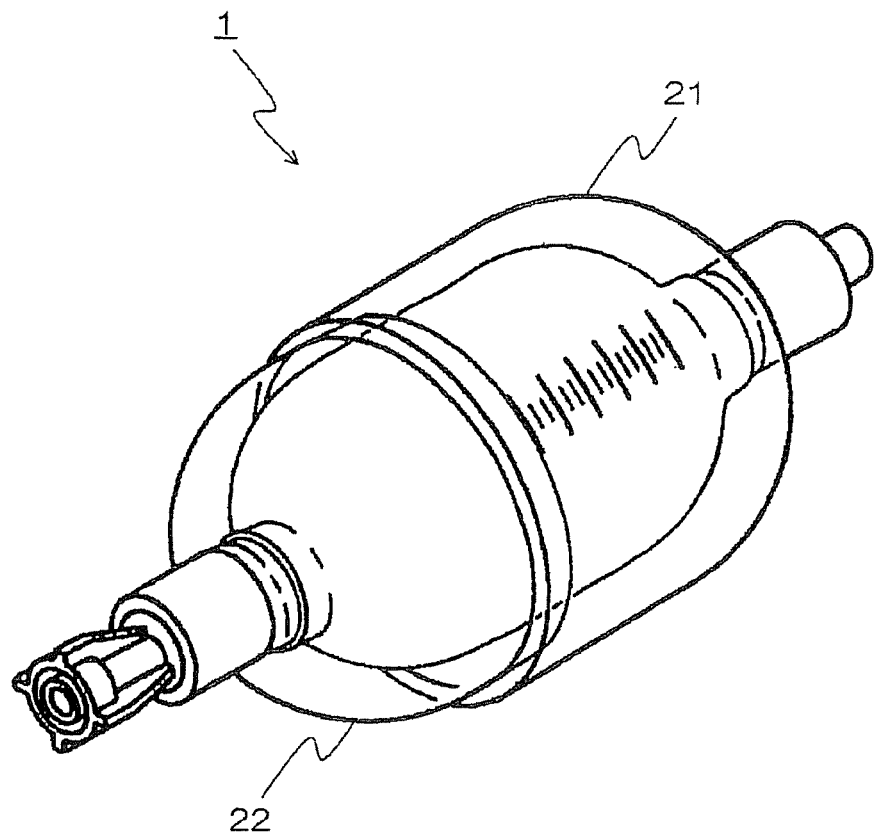
FIG. 3 is a perspective view of the continuous drug solution infusion device disclosed in FIG. 1.

The continuous drug solution infusion device of the present invention has at least two tubular members disposed in series along an infusion path for a drug solution and at least one expandable/contractible tubular member disposed between the tubular members. In this embodiment, the continuous drug solution infusion device 1 mainly has, as shown in FIGS. 1 and 2, a first tubular member 3, a second tubular member 4, and an expandable/contractible tubular member 5. The first tubular member 3 and the second tubular member 4 are disposed in series at an inlet end and an outlet end, respectively, of the drug solution infusion path. The expandable/contractible tubular member 5 is disposed between the first and second tubular members 3 and 4.

[First Tubular Member]

The first tubular member 3 has a substantially circular cylindrical shape and has a drug solution filling part 6 fitted therein. The drug solution filling part 6 is a stepped, substantially circular cylindrical member including a large-diameter portion 6a fitted to the inner peripheral surface of the first tubular member 3 and a small-diameter portion 6b formed integrally with the large-diameter portion 6a. The small-diameter portion 6b has a smaller outer diameter than that of the large-diameter portion 6a. The small-diameter portion 6b extends coaxially with the large-diameter portion 6a and is positioned to project to the outside of the device from the first tubular member 3. The large-diameter portion 6a has a recess 7 formed at an end thereof opposite to the small-diameter portion 6b. The recess 7 opens to the inside of the expandable/contractible tubular member 5. The small-diameter portion 6b and the large-diameter portion 6a have a central drug solution passage 8 extending therethrough in the axial direction and having a smaller diameter than that of the recess 7. The central drug solution passage 8 opens at the bottom of the recess 7 in the large-diameter portion 6a. A valve member 9 is provided in the opening of the central drug solution passage 8 that is located at the bottom of the recess 7. The valve member 9 functions as a check valve for preventing the back flow of the filled drug solution. In response to the valve member 9 separating from and being seated on the bottom of the recess 7, the central drug solution passage 8 is opened and closed. The valve member 9 may be a poppet valve that is usually used in conventional continuous drug solution infusion device. A retaining member 10 is provided at an intermediate position in the depth direction of the recess 7 to prevent the valve member 9 from falling out of the central drug solution passage 8 when it is moved to open the passage 8.

[Second Tubular Member]

Figure 4:
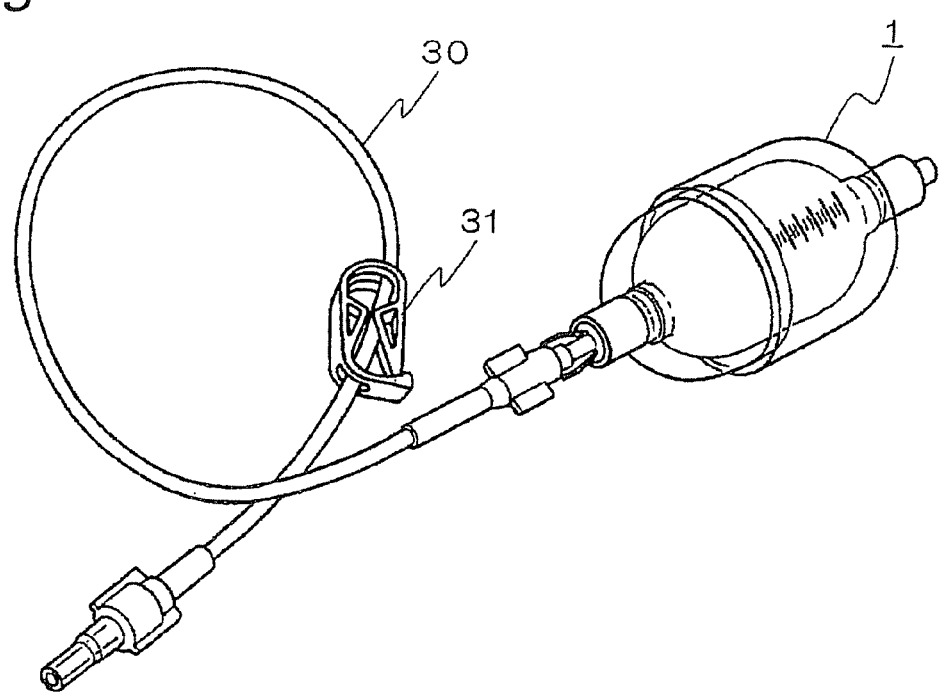
FIG. 4 is a perspective view of the continuous drug solution infusion device disclosed in FIG. 1, showing a state where a flexible tube is attached to a drug solution outlet part of the device.

The second tubular member 4 also has a substantially circular cylindrical shape similar to that of the first tubular member 3 and has a substantially circular cylindrical drug solution outlet part 11 fitted to the inner peripheral surface thereof. The drug solution outlet part 11 is connected with a male lure-lock connector 12. In this embodiment, the male lure-lock connector 12 is, as shown in FIG. 4, connected with an elongate flexible tube 30 having a length of 20 to 1,000 mm and an inner diameter of 0.1 to 0.5 mm. The flexible tube 30 is provided with a clamp 31 that opens and closes the passage in the flexible tube 30 to allow and cut off the outflow of a drug solution. A conventional catheter (not shown) is connected to the flexible tube 30. The catheter is connected to the interior of the patient's body. The flexible tube 30 is provided with a control passage (not shown) at the distal end (catheter-side end) thereof that reduces the flow rate of a drug solution to be infused into the patient's body to control the outflow time (0.5 to 10 hours).

[Expandable/Contractible Tubular Member]

The expandable/contractible tubular member 5 is made of an elastic material, e.g. a rubber material, which is sufficiently expandable in both the radial and axial directions thereof, and can accommodate a predetermined amount of drug solution (e.g. 40 to 250 cc in this embodiment).

In the continuous drug solution infusion device 1 of the present invention arranged as stated above, the expandable/contractible tubular member 5 is disposed between the first tubular member 3 and the second tubular member 4. Therefore, unlike in the conventional continuous drug solution infusion device in which a balloon is secured at both ends thereof to a single tube, the expandable/contractible tubular member 5 can be expanded and contracted not only in the radial direction but also in the axial direction. Consequently, the change in pressure due to the contraction of the expandable/contractible tubular member 5 can be suppressed, and a drug solution can be continuously administered into the patient's body substantially at a predetermined flow rate from the beginning to end of the infusion. Normally, the first tubular member 3 and the second tubular member 4 can be positioned close to each other. Therefore, the axial size of the device can be reduced. In addition, the drug solution storage capacity of the device can be increased.

[Protection Cover]

The continuous drug solution infusion device 1 in this embodiment has a protection cover 20 divided into two parts in the axial direction. The protection cover 20 can protect the expandable/contractible tubular member 5 when it expands. As illustrated in the figures, the protection cover 20 comprises a large-diameter outer cover 21 and a small-diameter inner cover 22 provided inside the outer cover 21. The outer cover 21 and the inner cover 22 are secured to the first tubular member 3 and the second tubular member 4, respectively, to cover the expandable/contractible tubular member 5. The outer cover 21 has a tubular portion 21a having a circular cylindrical surface extending substantially parallel to the center axis of the tubular members. The tubular portion 21a is open at both ends thereof. The outer cover 21 further has a substantially dome-shaped curved portion 21b extending radially inward from one end of the tubular portion 21a. The curved portion 21b has an opening formed at the top thereof to pass the first tubular member 3 therethrough. The inner cover 22 is similar in arrangement to the outer cover 21. That is, the inner cover 22 has a tubular portion 22a having a circular cylindrical surface extending substantially parallel to the center axis of the tubular members. The tubular portion 22a is open at both ends thereof. The inner cover 22 further has a substantially dome-shaped curved portion 22b extending radially inward from one end of the tubular portion 22a. The curved portion 22b has an opening formed at the top thereof to pass the second tubular member 4 therethrough. The outer cover 21 and the inner cover 22 are fixed to the first tubular member 3 and the second tubular member 4, respectively, at the openings of the curved portions 21b and 22b, with the first and second tubular members 3 and 4 extending through the respective openings. Dividing the protection cover 20 into two parts in the axial direction of the tubular members as stated above allows the expandable/contractible tubular member 5 to expand and contract in the axial direction. That is, at the time of filling a drug solution, the outer cover 21 and the inner cover 22 can move away from each other to allow the expandable/contractible tubular member 5 to fully expand in the axial direction to fill the drug solution to the maximum. Meanwhile, when the continuous drug solution infusion device 1 is in a normal inoperative state, the outer cover 21 and the inner cover 22 can move toward each other. At this time, substantially the whole inner cover 22 can be accommodated in the outer cover 21. Accordingly, the device can be made compact in the axial size, and it is possible to reduce the space required during storage and transportation as compared with the conventional device. At the same time, it is possible to reduce the cost of disposing of the device as a medical waste. It should be noted that the protection cover may be a simple circular cylindrical cover.

As shown in FIGS. 1 and 2, the outer and inner covers 21 and 22 of the protection cover 20 may be provided with separation-preventing stoppers that are engageable with each other. In this embodiment, two sets of stoppers 23 and 24 are provided at substantially the exact opposite positions along the diametrical direction of the tubular members. The stoppers 23 are formed by bending radially inward an end portion of the tubular portion 21a of the outer cover 21 on a side thereof opposite to the curved portion 21b. The stoppers 24 are formed by bending radially outward an end portion of the tubular portion 22a of the inner cover 22 on a side thereof opposite to the curved portion 22b. Thus, even when the expandable/contractible tubular member 5 is expanded to the maximum in the axial direction, the outer cover 21 and the inner cover 22 can be prevented from separating from each other in the axial direction by the mutual engagement of the stoppers 23 and 24. Accordingly, the drug solution can be filled to the maximum of the capacity of the device. The number of sets of stoppers is not particularly limited. A plurality of sets of stoppers may be disposed along the circumferential direction of the protection cover. There may be provided only one set of stoppers. In addition, the outer cover 21 and the inner cover 22 may be provided with annular stoppers, respectively, which extend over their entire circumferences.

Figure 5:
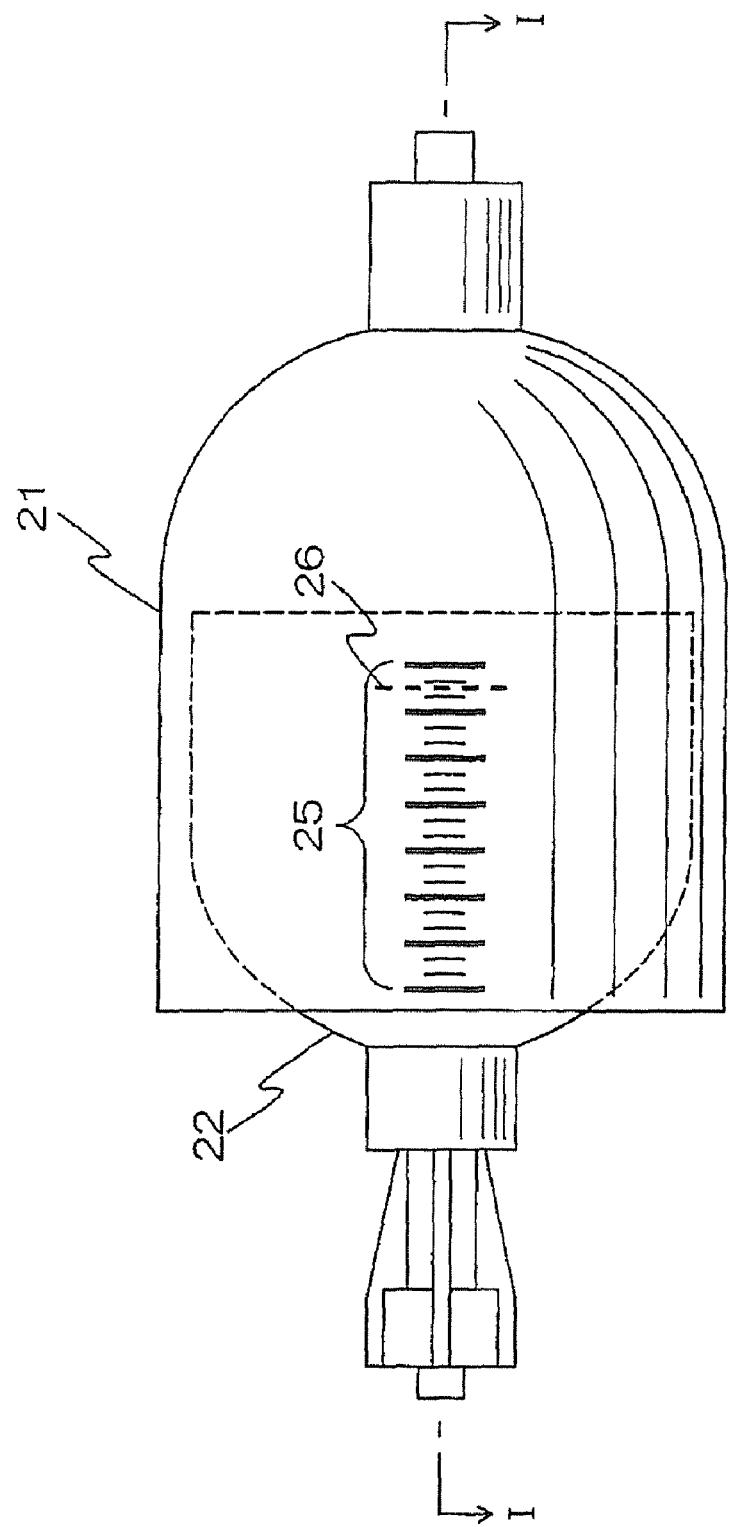
FIG. 5 is a front view of the continuous drug solution infusion device disclosed in FIG. 1, showing a state where an outer cover and an inner cover are positioned close to each other.
Figure 6:
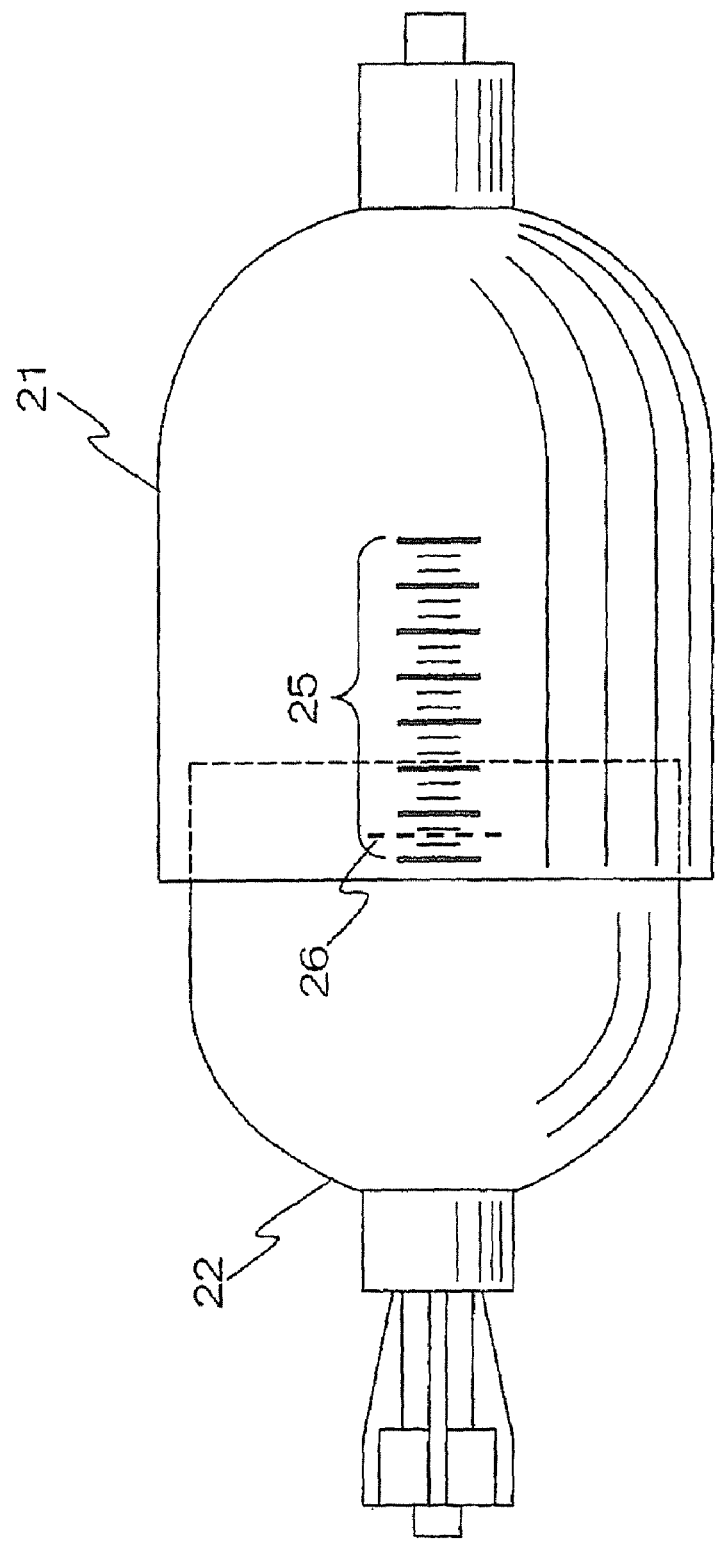
FIG. 6 is a front view of the continuous drug solution infusion device disclosed in FIG. 1, showing a state where the outer and inner covers are positioned away from each other.
Figure 7:
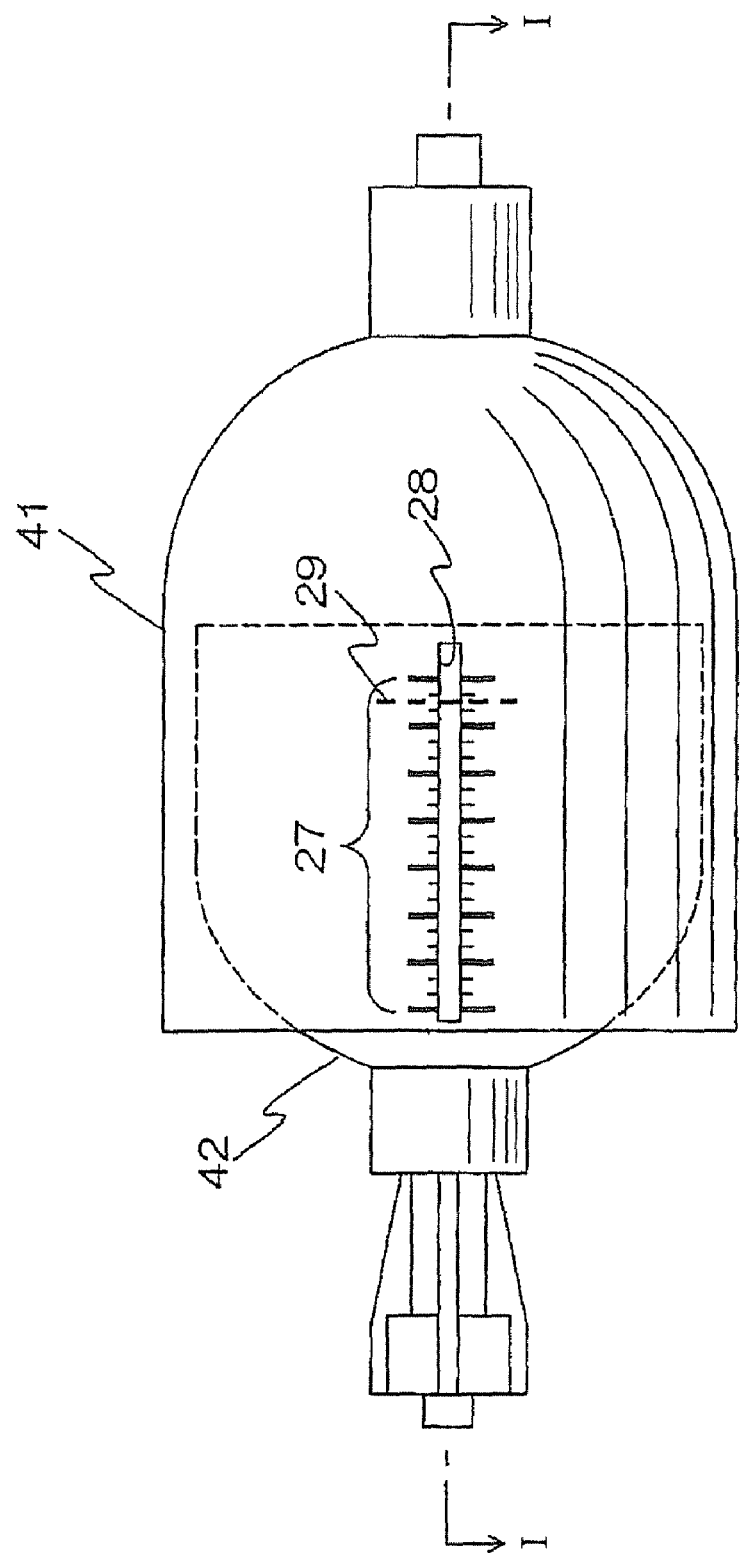
FIG. 7 is a front view of a continuous drug solution infusion device according to another embodiment of the present invention.

The protection cover 20 is formed from a transparent or semitransparent plastic material, for example, and may be provided with a combination of graduations and a reference line corresponding to the position of the graduations as a drug solution measuring means. Specifically, the arrangement may be as shown in FIG. 5. That is, graduations 25 are formed on the outer cover 21, and a reference line 26 is provided on the inner cover 22. Conversely, graduations 25 may be formed on the inner cover 22, and a reference line 26 on the outer cover 21. The following is an explanation of the function of the drug solution measuring means as arranged to have graduations 25 formed on the outer cover 21 and a reference line 26 provided on the inner cover 22. The explanation will be made with reference to FIGS. 5 and 6. When the continuous drug solution infusion device 1 is in a normal inoperative state, the expandable/contractible tubular member 5 is in a contracted state. Accordingly, the outer cover 21 and the inner cover 22 secured to the first and second tubular members 3 and 4, respectively, are located closest to each other (FIG. 5). As the device is filled with a drug solution, the expandable/contractible tubular member 5 expands in both the radial and axial directions, causing the outer cover 21 and the inner cover 22 to move away from each other (FIG. 6). While the filled drug solution is being infused into the patient's body, the expandable/contractible tubular member 5 gradually contracts. Consequently, the outer cover 21 and the inner cover 22 axially move back toward the respective positions where they are close to each other as shown in FIG. 5. At this time, the position of the reference line 26 relative to the graduations 25 also changes toward the position as shown in FIG. 5. The amount of drug solution remaining in the device can be measured easily by reading the changing position of the reference line 26 from the graduations 25. Accordingly, the drug solution administration control is facilitated. The drug solution measuring means is not limited to the illustrated embodiment. For example, the arrangement may be as shown in FIG. 7, wherein a slit 28 provided with graduations 27 is provided on an outer cover 41 in place of the graduations 25, and a reference line 29 is provided on an inner cover 42 in correspondence to the position of the slit 28. With this arrangement, the position of the reference line 29 seen through the slit 28 is read from the graduations 27. In this case, the protection cover may not necessarily be made transparent or semitransparent. It should be noted that the reference line is shown by a dotted line for the sake of explanation because it is provided on the inner cover 42. Although the graduations 25 and 27 are provided at regular intervals in the figures, they may be provided at irregular intervals.

The following is an explanation of the operation of the continuous drug solution infusion device in this embodiment. First, as shown in FIG. 1, the drug solution outlet part 11 of the device 1 of the present invention and the male lure-lock connector 12, which have already been sterilized, are connected to each other. Next, a doctor or the like fills the continuous drug solution infusion device 1 with a predetermined amount of a prescribed drug solution according to the patient's condition. For example, the device 1 is filled with a predetermined amount of a drug solution (e.g. a physiological saline, a glucose solution, an antibiotic solution, a sedative, an analgesic, heparin, etc.) from the drug solution filling part 6 by using a syringe or the like (not shown). The drug solution passes through the central drug solution passage 8, which is formed in the drug solution filling part 6, and opens the valve member 9 to flow into the expandable/contractible tubular member 5 through the recess 7. The drug solution is temporarily stored in the expandable/contractible tubular member 5. As described above, the expandable/contractible tubular member 5 has both ends secured to separate tubes, i.e. the first tubular member 3 and the second tubular member 4, respectively. Accordingly, as shown in FIG. 2, during the filling of the drug solution, the expandable/contractible tubular member 5 can be fully expanded not only in the radial direction of the tubes but also in the axial direction thereof.

After performing a required deaeration process, the doctor or the like secures the continuous drug solution infusion device 1 to the patient's body and connects, to the male lure-lock connector 12 attached to the drug solution outlet part 11, the flexible tube 30 and a catheter that communicates with the interior of the patient's body.

From this point of time, the drug solution is continuously infused into the patient's body by the contracting force of the expanded expandable/contractible tubular member 5. A high flow rate caused by the pressure of the expandable/contractible tubular member 5 is limited to a low level by the control passage provided at the distal end of the flexible tube 30. In addition, because the expandable/contractible tubular member 5 is expanded not only in the radial direction but also in the axial direction, the change in pressure due to the contraction of the expandable/contractible tubular member 5 is suppressed. Accordingly, the drug solution can be continuously infused into the patient's body for a long period of time substantially at a predetermined flow rate from the beginning to end of the infusion. During the administration of the drug solution, the amount of drug solution remaining in the device can be readily measured by the function of the drug solution measuring means (the graduations 25 and the reference line 26, etc.) stated above. Accordingly, the drug solution administration control is facilitated.

The drug solution may be previously filled in the continuous drug solution infusion device 1. Alternatively, the above-described filling of the drug solution may be performed after the device has been secured to the patient's body. The capacity of the continuous drug solution infusion device, infusion duration, etc. should be previously selected in accordance with the patient's condition.

The continuous drug solution infusion device of the present invention can be used again by repeating the above-described operation but may be thrown away after being used once.

Second Embodiment

In the foregoing first embodiment, both the outer and inner covers 21 and 22 of the protection cover 20 have a circular radial section. In the second embodiment of the present invention, the outer cover 21 is replaced with an outer cover having at least one flat portion in a section thereof taken in the radial direction of the tubular members. This prevents rolling of the device during use or during storage or transportation.

Third Embodiment

In a third embodiment of the present invention, the outer cover 21 and the inner cover 22 in the first embodiment are replaced respectively with an outer cover having at least one flat portion in a section thereof taken in the radial direction of the tubular members and an inner cover having a flat portion corresponding to the flat portion of the outer cover. The inner cover is fitted in the outer cover with their flat portions facing each other. With this structure, the outer cover and the inner cover can be prevented from rotating relative to each other, and it is possible to prevent twisting of the expandable/contractible tubular member 5 and to prevent incorrect measurement with the drug solution measuring means provided in the protection cover.

Fourth Embodiment

Figure 8:
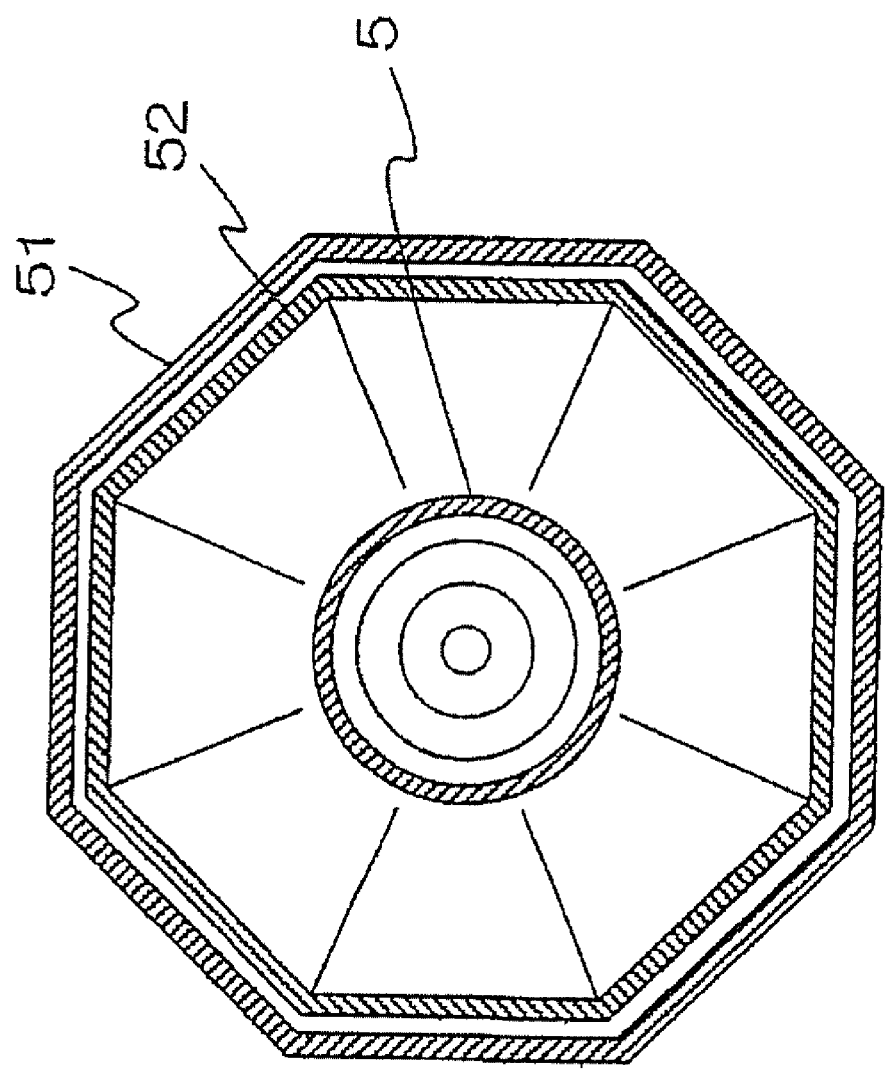
FIG. 8 is a diagram showing a radial section of a protection cover used in a continuous drug solution infusion device according to still another embodiment of the present invention.

In a fourth embodiment of the present invention, the outer cover 21 and the inner cover 22 in the first embodiment are replaced respectively with an outer cover 51 having a polygonal radial sectional shape and an inner cover 52 having a polygonal radial sectional shape so as to be fittable in the outer cover 51. Examples of such a radial sectional shape of the outer and inner covers 51 and 52 include a regular octagonal sectional shape as shown in FIG. 8. In this case, it is possible to prevent rolling of the device during use or during storage or transportation and to prevent relative rotation between the outer cover 51 and the inner cover 52 even more effectively.

INDUSTRIAL APPLICABILITY

The continuous drug solution infusion device of the present invention is also applicable to emergency medical care in addition to ordinary illness care and terminal care. In addition, the continuous drug solution infusion device is applicable to analgesia, sedation, detoxification, antipyresis, nutritional supplement, etc.

The invention claimed is:

1. A continuous drug solution infusion device comprising:
at least two tubular members disposed in series along an infusion path for a drug solution; and
at least one expandable/contractible tubular member disposed between said tubular members; and
a protection cover provided on the tubular members at both ends of said infusion path for the drug solution so as to cover said expandable/contractible tubular member, said protection cover comprising an outer cover having an open end, and an inner cover having an opposing open end disposed inside the open end of said outer cover, said outer cover and said inner cover being capable of moving toward and away from each other in a longitudinal axial direction of said tubular members.

2. The continuous drug solution infusion device of claim 1, wherein said tubular members comprise:
a first tubular member disposed at an inlet-side end of said infusion path for the drug solution; and
a second tubular member disposed at an outlet-side end of said infusion path for the drug solution;
said expandable/contractible tubular member being a single expandable/contractible tubular member disposed between said first tubular member and second tubular member.

3. The continuous drug solution infusion device of claim 1, wherein said protection cover includes drug solution measuring means.

4. The continuous drug solution infusion device of claim 3, wherein said protection cover is made of a transparent or semitransparent material;
said drug solution measuring means comprising:
graduations provided on one of said outer cover and inner cover; and
a reference line provided on the other of said outer cover and inner cover in correspondence to a position of said graduations.

5. The continuous drug solution infusion device of claim 3, wherein said drug solution measuring means comprises:
a slit provided with graduations, said slit being provided on said outer cover; and
a reference line provided on said inner cover in correspondence to a position of said slit.

6. The continuous drug solution infusion device of claim 1, wherein said outer cover and inner cover of said protection cover include separation-preventing stoppers which are engageable with each other.

7. The continuous drug solution infusion device of claim 1, wherein said outer cover has at least one flat portion in a section thereof taken in a radial direction of said tubular members.

8. The continuous drug solution infusion device of claim 1, wherein said inner cover has a flat portion corresponding to a flat portion of said outer cover, said inner cover being fitted in said outer cover with their flat portions facing each other.

9. The continuous drug solution infusion device of claim 1, wherein said outer cover has a polygonal section taken in a radial direction, and said inner cover has a polygonal section so as to fit in said outer cover.

10. The continuous drug solution infusion device of claim 2, wherein said protection cover includes drug solution measuring means.

11. The continuous drug solution infusion device of claim 10, wherein said protection cover is made of a transparent or semitransparent material;
said drug solution measuring means comprising:
graduations provided on one of said outer cover and inner cover; and
a reference line provided on the other of said outer cover and inner cover in correspondence to a position of said graduations.

12. The continuous drug solution infusion device of claim 10, wherein said drug solution measuring means comprises:
a slit provided with graduations, said slit being provided on said outer cover; and
a reference line provided on said inner cover in correspondence to a position of said slit.

13. The continuous drug solution infusion device of claim 2, wherein said outer cover and inner cover of said protection cover include separation-preventing stoppers which are engageable with each other.

14. The continuous drug solution infusion device of claim 2, wherein said outer cover has at least one flat portion in a section thereof taken in a radial direction of said tubular members.

15. The continuous drug solution infusion device of claim 2, wherein said inner cover has a flat portion corresponding to a flat portion of said outer cover, said inner cover being fitted in said outer cover with their flat portions facing each other.

16. The continuous drug solution infusion device of claim 2, wherein said outer cover has a polygonal section taken in a radial direction, and said inner cover has a polygonal section so as to fit in said outer cover.

17. A continuous drug solution infusion device comprising:
   two tubular members disposed in series along an infusion path for a drug solution; and
   an expandable/contractible tubular member disposed between the two tubular members; and
   a protection cover surrounding the expandable/contractible tubular member, the protection cover comprising two protection cover members that together define an overall dimension of the protection cover in a longitudinal axial direction of said tubular members, and the two protection cover members being movable away from each other to increase the overall dimension of the protection cover as the expandable/contractible tubular member expands, and movable toward each other to decrease the overall dimension of the protection cover as the expandable/contractible tubular member contracts.

18. The continuous drug solution infusion device of claim 17, wherein each of the two protection cover members is coupled at one end to one of the two tubular members, and is coupled at an opposing end to the other of the two plastic protection cover members.

19. The continuous drug solution infusion device of claim 18, wherein at least one of the two protection cover members is indirectly coupled at one end to one of the two tubular members.

20. A continuous drug solution infusion device comprising:
   at least two tubular members disposed in series along an infusion path for a drug solution; and
   at least one expandable/contractible tubular member disposed between said tubular members; and
   a protection cover provided on the tubular members at both ends of said infusion path for the drug solution so as to cover said expandable/contractible tubular member, said protection cover comprising an outer cover and an inner cover disposed inside said outer cover, a distal end of said outer cover and a proximal end of said inner cover being capable of moving toward and away from each other in an longitudinal axial direction of said tubular members.

* * * * *